United States Patent [19]

Reddy et al.

[11] Patent Number: 5,554,523
[45] Date of Patent: Sep. 10, 1996

[54] NUCLEIC ACID SEQUENCES ENCODING HUMAN LEUCINE-ZIPPER PROTEIN-KINASE

[75] Inventors: Usharani Reddy, North Wales; David Pleasure, Wynnewood, both of Pa.

[73] Assignee: Children's Hospital of Philadelphia, Philadelphia, Pa.

[21] Appl. No.: 205,018

[22] Filed: Mar. 1, 1994

[51] Int. Cl.$^6$ .............................. C12N 1/20; C12N 15/00; C12N 9/12
[52] U.S. Cl. .................. 435/194; 435/252.3; 435/320.1; 536/23.2
[58] Field of Search ................................. 435/194, 320.1, 435/252.3; 536/23.2

[56] References Cited

PUBLICATIONS

Asano et al., "Domains Responsible for the Differntial Targeting of Glucose Transporter Isoforms", *J. Biol. Chem.* 267: 19636–19641 (1992).

Forman et al., "A Domain Containing Leucine–Zipper–Like Motifs mediate novel In Vivo Interactions Between the Thyroid hormone and Retinoic Acid Receptors", *Molecular Endocrinology* 3: 1610–1626 (1989).

Pleasure et al., "Pure, Postmitotic, Polarized Human Neurons Derived from NTera 2 Cells Provide a System for Expressing Exogenous Proteins in Terminally Differentiated Neurons", *J. Neuroscience* 12: 1802–1814 (1992).

Wernet et al., "the cDNA of The Two Isoforms of Bovine cGMP–Dependent Protein Kinase",*FEBS*251: 191–196 (1989).

Younkin et al., "Inducible Expression of Neuronal Glutamate Receptor Channels in the NT2 Human Cell Line", *Proc. Natl. Acad. Sci. USA* 90: 2174–2178 (1993).

*Primary Examiner*—Robert A. Wax
*Assistant Examiner*—Keith D. Hendricks
*Attorney, Agent, or Firm*—Woodcock Washburn Kurtz Mackiewicz & Norris

[57] ABSTRACT

A novel protein kinase, leucine-zipper protein kinase, 668 amino acids in length is provided by the present invention. This protein kinase is localized to the human brain. Nucleic acid sequences encoding the protein kinase are also provided.

6 Claims, 7 Drawing Sheets

1    agcatccggagcggagctgcagcagcggccgcgcctttgtgctgcggccgagcccccgagggcccagtgtt

73   CACCATCATACCAGGGGCCAGAGGGCCGATGGCTTGCCTTCCATGAGACCCGAACACCCTCTCCTTCCTTTGGGG
                              M  A  C  L  H  E  T  R  T  P  S  P  S  F  G

145  GCTTTGTGTCTACCCTAAGTGTGAGGCATCCATGCGCAAGCTGGACCCAGAGACTTCTGACTGCACTCCCGAGA
     G  F  V  S  T  L  S  E  A  S  M  R  K  L  D  P  D  T  S  D  C  T  P  E

217  AGGACCTGACGCCTACCCATGTCCTGCAGCTACACATGAGCAGGATGCAGGGGCCCAGGGGAGCAGCTGGGT
     K  D  L  T  P  T  H  V  L  Q  L  H  E  Q  D  A  G  G  P  G  G  A  A  G

289  CACCCTGAGAGTCGGGCGGCATCCAGAGTTCGAGCTGACGAGGTGCGACTGCCAGAGTGGCCAGTGGCTTCC
     S  P  E  S  R  A  S  R  V  R  A  D  E  V  R  L  Q  C  Q  S  G  S  G  F

361  TTGAGGGCCTCTTTGGCTGCCTGCGCCCTGTCTGGACCATGATTGGCAAGCCTACTCCACTGAGCACAAGC
     L  E  G  L  F  G  C  L  R  P  V  W  T  M  I  G  K  A  Y  S  T  E  H  K

433  AGCAGCAGGAAGACCTTTGGGAGGTCCCCCTTTGAGGAAATCCTGGACCTGCAGTGGGGTGGGGCTCAGGGGCCC
     Q  Q  Q  E  D  L  W  E  V  P  F  E  E  I  L  D  L  Q  W  V  G  S  G  A

505  AGGGTGCTGTCTTCCTGGGGCTTCCACGGGGAGGAGGTGGCTGTGAAGAAGTGCGAGACCTCAAAGAAA
     Q  G  A  V  F  L  G  R  F  H  G  E  E  V  A  V  K  K  V  R  D  L  K  E

577  CCGACATCAAGCACTTGCAAAGCTGAAGCACCCCAACATCATCACTTTCAAGGGTGTGTGCACCCAGGCTC
     T  D  I  K  H  L  R  K  L  K  H  P  N  I  I  T  F  K  G  V  C  T  Q  A

FIG. 1A

```
649   CCTGCTACTGCATCCTCATGGAGTTCTGCGCCCAGGGCCAGCTGTATGAGGTACTGGGGCTGGCCGCCCTG
      P  C  Y  C  I  L  M  E  F  C  A  Q  G  Q  L  Y  E  V  L  R  A  G  R  P

721   TCACCCCCTCCTTACTGGTTGACTGGTGTCCATGGGCATCGCTGGTGGCATGAACTACCTGCACCTGCACAAGA
      V  T  P  S  L  L  V  D  W  S  M  G  I  A  G  G  M  N  Y  L  H  L  H  K

793   TTATCCACAGGGATCTCAAGTCACCCAACATGCTAATCACCTACGACGATGTGGTGAAGATCTCAGATTTTG
      I  I  H  R  D  L  K  S  P  N  M  L  I  T  Y  D  D  V  V  K  I  S  D  F

865   GCACTTCCAAGGAGCTGAGTGACAAGAGCACCAAGATGTCCTTTGCAGGGACAGTAGCCTGGATGGCCCCTG
      G  T  S  K  E  L  S  D  K  S  T  K  M  S  F  A  G  T  V  A  W  M  A  P

937   AGGTGATCCGCAATGAACCTGTGTCTGAGAAGGTCGACATCTGGTCCTTTGGCGTGGTGCTATGGGAACTGC
      E  V  I  R  N  E  P  V  S  E  K  V  D  I  W  S  F  G  V  V  L  W  E  L

1009  TGACTGGTGAGATCCCCTACAAAGACGTAGATTCCTCAGCTATTATCTGGGGTGTGGGAAGCAACAGTCTCC
      L  T  G  E  I  P  Y  K  D  V  D  S  S  A  I  I  W  G  V  G  S  N  S  L

1081  ATCTGCCCGTGCCCTCCAGTTGCCCAGATGGTTTCAAGATCCTGCTTCGCCTGGAATAGCAAACCAC
      H  L  P  V  P  S  S  C  P  D  G  F  K  I  L  L  R  Q  C  W  N  S  K  P

1153  GAAATCGCCCATCATTCCGACAGATCCTGCTGCATCTGGACATTGCCTCAGCTGATGTACTCTCCACACCCC
      R  N  R  P  S  F  R  Q  I  L  L  H  L  D  I  A  S  A  D  V  L  S  T  P
```

FIG. 1B

```
1225  AGGAGACTTACTTTAAGTCCCAGGCAGAGTGGCGGGAAGAAGTAAAACTGCACTTTGAAAAGATTAAGTCAG
       Q  E  T  Y  F  K  S  Q  A  E  W  R  E  E  V  K  L  H  F  E  K  I  K  S

1297  AAGGGACCTGTCTGCACCGCCTAGAAGAGGAACTGGTGATGAGGAGGAGCTCAGACACGCCCCTGG
       E  G  T  C  L  H  R  L  E  E  E  L  V  M  R  R  R  E  E  L  R  H  A  L

1369  ACATCAGGGAGCACTATGAAGAGAAGCTGGAGAGAGCCAACAACCTGTATATGGAACTTAATGCCCTCATGT
       D  I  R  E  H  Y  E  R  K  L  E  R  A  N  N  L  Y  M  E  L  N  A  L  M

1441  TGCAGCTGGAACTCAAGGAGGAGAGGGAGCTGCTCAGGCGAGAGCAAGCTTTAGAGCCGAGGTGCCCAGGCCTGC
       L  Q  L  E  L  K  E  E  R  E  L  L  R  R  E  Q  A  L  E  R  R  C  P  G  L

1513  TGAAGCCACACCCCTTCCCGGGCCTCCTGCATGGAAACACAATGTGAGAAGCTTATCAAGAAGAGGAATGTGC
       L  K  P  H  P  S  R  G  L  L  H  G  N  T  M  E  K  L  I  K  K  R  N  V

1585  CACAGAATCTGTCACCCCATAGCCAAGGCGGAGTCTCTTTGCTCCCTAAACTAGATG
       P  Q  N  L  S  P  H  S  Q  R  P  D  I  L  K  A  E  S  L  L  P  K  L  D

1657  CAGCCCCTGAGTGGGGTGGGGCTTCCTGGGGTGTCCTAAGGCCCCCCTCACCAGGACGGAGTCGCCGTGGCA
       A  A  L  S  G  V  G  L  P  G  C  P  K  A  P  P  S  P  G  R  S  R  R  G

1729  AGACCCGTCACCGGCAAGGCGCCAGCGCGTGTGGGGAGCTGCCTGCCTCGGCTTCGTACAGCTGTGCCAC
       K  T  R  H  R  K  A  S  A  K  G  S  C  G  D  L  P  G  L  R  T  A  V  P
```

FIG. 1C

```
1801  CCCATGAACCTGGAGGACCAGGAAGCCCAGGGGGACCCTCAGCCTGGGAGGCCTGCCCTC
       P  H  E  P  G  G  P  G  S  P  G  G  L  G  G  G  P  S  A  W  E  A  C  P

1873  CCGCCCTCCGTGGGCTTCATCATGACCTCCTGCTCCGCAAAATGTCTTCATCGTCCCCAGACCTGCTGTCAG
       P  A  L  R  G  L  H  H  D  L  L  R  K  M  S  S  S  P  D  L  L  S

1945  CAGCACTAGGGTCCCGGGGATCCCGGAGCTGGGAGATCCTGGCTCCACCACCTCCGGCCCGGG
       A  A  L  G  S  R  G  R  G  A  T  G  G  A  G  D  P  G  S  P  P  P  A  R

2017  GTGACACCCCACCAAGTGAGGGCTCCACCCCCTGGCTCCACCAGCCCAGATTCACTGGGAGCCAAAGGGGA
       G  D  T  P  P  S  E  G  S  P  P  G  S  T  S  P  D  S  P  G  E  P  P  K  G

2089  ACCACCTCCTCCAGTAGggcctggtgaaggtgtgggcttctgggaactggaaggaaggaggacctcaggccg
       N  H  L  L  Q  .  (SEQ ID NO: 2)

2161  gggaggaagccgggctgggtcccagcacttgaccccatctgcactgctgtacagggctgcgcgtcacccgaag 2233  tcagaaacgtggcatctctcatcggaagagaggaggaggtagacagtgaagtagagctgacatcaagcca 2305  gaggtggcctcagagcctgaacatgcgcagtcactacttcagctcagagaatccatcagatgggga 2377  ggaaggcacagctagtgaaccttccccccagtggcacacctgaagttggcagcaccaacactgatgagcggcc
```

FIG. ID

```
2449  agatgagcgggtctgatgacatgtgctcccagggctcagaaatcccactgacccacctccttcagaggtcat
2521  ccctggccctgaacccagctccctgcccattccacaccaggaacttctcagagagcggggccctcccaattc
2593  tgaggactcagactgtgacagcactgaattggacaactccaacagcgttgatgccttgcgccccagcttc
2665  cctccctccatgaaagccactcgtattccttgtacatagagaaatatttatatggattatatatatacat
2737  atatatatatatgcgccacataatcaacagaaagatggggctgtcccagccgtaagtcaggctcgaggga
2809  gactgatcccctgaccaattcacctgataaactctaggacactggcagctgtggaaatgaggcacag
2881  ccgtagagctgtggctaaggcaagcccccttcctgccccaccccattccttatattcagcaagcaacaaggc
2953  aatagaaaagccagggttgtctttatattcttatcccaaataataggggggtggggggaggggcggtggga
```

FIG. IE

```
3025  gggcaggagagaaaaccactagactgcacttttctgttcctgttactctgttacacatttgcacttgg
3097  gaggaggaggctaaggctgggtcctccctctgagtttctcaggtggcaatgtaactcatttttgtcc
3169  caccattatctctctgcccaagccctgtcttaaggcccaggggggaggttaggagactgatagcatgtgat
3241  ggctcaggctgaagaaccggggttctgtttaagtccctgctttatcctggtgcctgattggggtggggact
3313  gtcctactgtaacccctgtgaaaaaccttgaaaataacactccatgcaggaaaaaaaaaaaaaaaaaa
3385  aaaaggaattcgatatcaagcttatcgataccgtcgacctcg    (SEQ ID NO: 1)
```

FIG. 1F

NUCLEIC ACID SEQUENCES ENCODING HUMAN LEUCINE-ZIPPER PROTEIN-KINASE

REFERENCE TO GOVERNMENT GRANTS

The work present herein was supported in part by National Institute of Health grants NS08075, NS25044 and NS31102. The United States government may have certain rights in the invention.

FIELD OF THE INVENTION

This invention is directed to a novel protein-kinase, nucleic acid sequences encoding the same and methods related thereto.

BACKGROUND OF THE INVENTION

Protein kinases regulate various cellular responses to changing environmental conditions. Protein kinases fall into two general classes: those protein kinases that transfer phosphate to serine or threonine and those proteins that transfer phosphate to tyrosine (Krebs and Beavo, *Annu. Rev. Biochem* 48: 923–959 (1979)). A few protein kinases, such as weel, now appear to be capable of phosphorylating both ser/threonine and tyrosine (Lindberg et al., *Trends Biochem Sci* 17: 114–119 (1992)). Phosphorylation is of particular significance in controlling mitogenesis and cellular differentiation. Receptors for a number of polypeptide growth factors are transmembrane tyrosine kinases (Yarden and Ullrich, *Annu. Rev. Biochem* 57: 443–478 (1988)), which in turn stimulate serine/threonine kinases such as protein kinase C, MAP kinase and p74$^{raf}$ (Hunter et al., *Nature* 311: 480–483 (1984); Morrison et al., *Cell* 58: 649–657 (1989); Rossomondo et al., *Proc. Natl. Acad. Sci. USA* 86: 6940–6943 (1989)).

Protein kinases, and especially the overexpression thereof, have been found to be linked to hyperproliferation of cells and metastasis. Many protein kinases were first identified as the products of oncogenes and still constitute the largest family of known oncogenes. Lindberg and Hunter, *Mol. and Cell. Biol.*, 10(11): 6316–6324 (1990).

Mutations of genes encoding members of the protein kinase family which are involved in the regulation of neuroblastic proliferation, differentiation and survival play a role in the etiology of human central nervous system tumors. Thus, it is highly desirable to gain a greater understanding of this class of proteins, as well as to use such greater understanding to limit or inhibit the effects that these proteins have on cellular hyperproliferation.

SUMMARY OF THE INVENTION

There is provided by the present invention a cDNA sequence encoding a novel protein kinase, leucine-zipper protein kinase (zpk), and the protein encoded thereby.

There are provided by the present invention recombinant constructs encoding leucine-zipper protein kinase.

There are provided by the present invention novel methods of use and diagnosis for leucine-zipper protein kinase and cDNA coding for leucine-zipper protein kinase.

BRIEF DESCRIPTION OF THE DRAWINGS

FIGS. 1A–1F. Nucleotide sequence (SEQ ID NO: 1) and putative amino acid sequence (SEQ ID NO: 2) of leucine-zipper protein kinase. Amino acid numbering starts with the initiation codon.

FIGS. 2A(a)–2A(b) represent Northern blots hybridized to α-[$_{32}$P] labeled leucine zipper protein kinase cDNA from human adult tissue FIG. 2A(a) and from human fetal tissue FIG. 2A(b).

DETAILED DESCRIPTION OF THE INVENTION

Figure 2A:
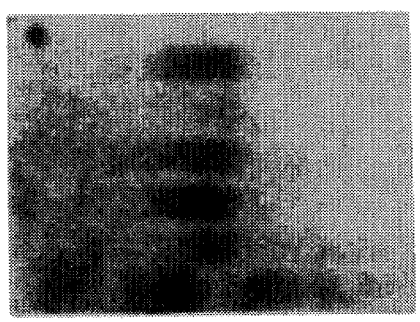
FIGS. 2A(a)–2B(b). Northern blots of expression of leucine zipper protein kinase in human tissue.
Figure 2B:
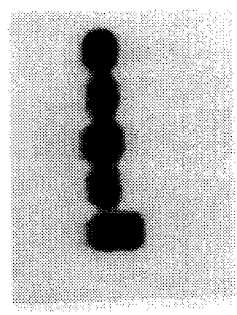
FIGS. 2B(a)–2B(b) represent Northern blots hybridized to α-[$_{32}$P] labeled β-actin cDNA from human adult tissue FIG. 2B(a) and from human fetal tissue FIG. 2B(b).
Figure 2A:
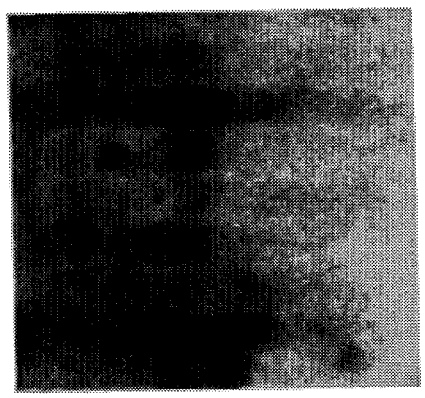
Figure 2B:

A novel member of the protein serine/threonine kinase family, leucine-zipper protein kinase is provided by the present invention. As used herein, the term leucine-zipper protein kinase (zpk) refers to a protein having an amino acid sequence substantially homologous to at least a portion of the amino acid sequence set forth in SEQ ID NO: 2. In accordance with the present invention, the term "homologous" refers to a one to one correlation between the sequences of two polypeptides or oligonucleotides. Of course, 100% homology is not required in all cases. In some instances polypeptides of the present invention may be substantially homologous to the amino acid sequence set forth in SEQ ID NO: 2. Substantial homology requires only that the essential nature of the polypeptide, i.e. folding characteristics and unique features such as the leucine zipper are preserved. Thus, modifications of the leucine-zipper protein kinase are anticipated and are within the scope of the present invention. These modification may be deliberate, as through site directed mutagenesis, or may be accidental as through mutations in host which are producers of the protein. In some embodiments of the present invention polypeptides of the present invention may be at least about 75% homologous to the sequence set forth in SEQ ID NO: 2. In other embodiments of the present invention polypeptides may be at least about 85% homologous to the sequence set forth in SEQ ID NO: 2. In yet other embodiments of the present invention polypeptides may be at least about 95% homologous to the sequence set forth in SEQ ID NO: 2. It is also anticipated that certain non-commonly occurring amino acids may be substituted for commonly occurring counterparts to confer desirable characteristics to the resulting polypeptide.

Furthermore, it is contemplated in some aspects of the present invention that a polypeptide may comprise only a portion of the sequence set forth in SEQ ID NO: 2. This may be the case, for example, for a chimeric protein encompassing active or otherwise desirable portions of a number of proteins. A portion may also refer to a truncated polypeptide, be it substantially truncated or only slightly truncated. Such truncated polypeptides may be the result of an idiosyncracy in the mode of production which results in truncation of amino acids from a terminal end, or a finding that the truncated polypeptide works as well or better than the full-length protein. For example, it might be found that the region directly surrounding the protein kinase domain at amino acids 231–243 is especially active.

Of course, in still other aspects of the present invention, the full-length protein, as set forth in SEQ ID NO: 2, is contemplated.

The leucine-zipper protein kinase of the present invention, depending on the pH of its environment, if suspended or in solution, or of its environment when crystallized or precipitated, if in solid form, may be in the form of pharmaceutically acceptable salts or may be in neutral form. The free amino acid groups of the protein are, of course, capable of forming acid addition salts with, for example, organic acids such as hydrochloric, phosphoric, or sulfuric acid; or with organic acids such as, for example, acetic, glycolic, succinic, or mandelic acid. The free carboxyl groups are capable of forming salts with bases, including inorganic bases such as sodium, potassium, or calcium hydroxides, and such organic bases as piperidine, glucosamine, trimethylamine, choline, and caffeine. In addition, the protein may be modified by combination with other biological materials such as lipids and saccharides, or by side chain modifications such as acetylation of amino groups, phosphorylation of hydroxyl side chains or oxidation of sulfhydryl groups.

The leucine-zipper protein kinase is preferably purified and isolated. "Purified" and "isolated" as the terms are used herein, are meant to refer to molecules which have been purified or synthesized so as to be substantially homogenous. The terms do not exclude the possibility that certain impurities may be present in the composition as long as the essential nature of the protein is intact.

Tissue distribution analysis indicated that leucine-zipper protein kinase is present in the brain, more so in the adult than in the fetal brain based upon the detection of a 3.4 Kb mRNA transcript. A smaller mRNA transcript, about 3.2 Kb was detected in kidney and skeletal muscle. Adult lung tissue expressed both transcripts at a very low level. In fetal tissue, the only definite transcript seen is in the brain. These results can be seen in FIGS. 2A(a)–2B(b).

The cDNA sequence of a novel leucine-zipper protein kinase is also provided by the present invention. The cDNA has a long open reading frame encoding 668 amino acids. The methionine codon at nucleotides 99–101 matches Kozak's consensus sequence for the initiation of translation. Kozak *Nucleic Acid Res* 9: 5233–5252 (1981). The polyadenylation signal AATAAC was found at nucleotides 3347–3352. Wickens and Stephenson, *Science* 226:1045–1051 (1984). The 5' cap site is CATCCG, 90 base pairs from the initiation start site.

Homology searches of leucine-zipper protein kinase with the nucleotide and amino acid databases showed no homology to any known protein kinase family. Leucine-zipper protein kinase is most similar to serine/threonine specific protein kinases. The leucine zipper protein kinase protein is believed to be a "non-receptor type kinase" based on its lack of a transmembrane domain. The consensus sequences for the ATP-binding site, Gly-Xaa-Gly-Xaa-Xaa-Gly and Lys residues are found at positions 537–544 and 548, respectively. The protein kinase domain was found to be at position 231–243. Taylor, et al., *Annu. Rev. Cell Biol.*, 8, 429–462 (1992). At the C-terminus of the protein, there was two overlapping sites of leucine zipper motif (leucine at every seventh amino acid), at position 442–468. A putative endoplasmic reticulum-targeting sequence was located at residues 415–418 (Pelham, H. R. B., *Annu. Rev. Cell Biol.*, 5, 1–23 (1989).

Comparison with other members of the family of protein kinases indicate that leucine-zipper protein kinase has a number of novel features. First, the glycine rich loop in leucine zipper protein kinase is present towards the C-terminus of the catalytic domain, whereas in other protein kinases it is present near the N-terminus.

Endoplasmic reticulum targeting sequences (REEL) have been identified in both soluble; Pelham, H.R.B., *Annu. Rev. Cell. Biol.*, 5, 1–23 (1989); and transmembrane; Jackson, et al., *EMBO J.*, 9, 3153–3162 (1990) endoplasmic reticulum proteins. A lysine rich motif at the cytoplasmically-exposed C-terminus of some transmembrane proteins was described which conferred endoplasmic reticulum localization, although a more complex retention signal at the C-terminus has also be postulated. Gabathuler and Kvist, *J. Cell Biol.*, 111, 1803–1810 (1990). Leucine-zipper protein kinase contains an endoplasmic reticulum targeting sequence which is located from amino acid 415–416, rather than at the extreme C-terminus of the protein.

Leucine-zipper protein kinase is also unique in that it contains a leucine-zipper motif, a sequence in which leucines occur at every seventh amino acid. Leucine-zippers contribute to targeting of various proteins (eg. glucose transporters, Asano, et al., *J. Biol. Chem.*, 267, 19636–19641 (1992)) and permit dimerization of various cytoplasmic hormone receptors and enzymes. Forman, et al., *Mol Endocrinol*, 3, 1610–1626 (1989). Leucine zippers are also a common feature of protein transcription factors, where they permit homo- or heterodimerization resulting in tight binding to DNA strands.

A leucine-zipper motif has been reported only once previously in a protein kinase, the bovine cGMP-dependent protein kinase, which has a leucine-isoleucine zipper motif at its N-terminus. Wernet, et al., *FEBS*, 251, 191–196 (1989).

Leucine-zipper protein kinase can be routinely synthesized in substantially pure form by standard techniques well known in the art, such as commercially available peptide synthesizers and the like.

Additionally, leucine-zipper protein kinase can be efficiently prepared using any of numerous well known recombinant techniques such as those described in U.S. Pat. No. 4,677,063 which patent is incorporated by reference as if fully set forth herein. Briefly, most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides additional markers which can be either retained or destroyed in constructing the desired vector. Commonly used procaryotic control sequences include promoters for transcription initiation, optionally with an operator, along with ribosome binding site sequences, include such commonly used promoters as the beta-lactamase (penicillinase) and lactose (lac) promoter systems (Chang, et al., *Nature* (1977) 198:1056) and the tryptophan (trp) promoter system (Goeddel, et al. *Nucleic Acids Res* (1980) 8:4057) and the lambda derived PL promoter and N-gene ribosome binding site (Shimatake, et al., Nature (1981) 92:128).

In addition to bacteria, eucaryotic microbes, such as yeast, may also be used as hosts. Laboratory strains of *Saccharomyces cerevisiae*, Baker's yeast, are most used although a number of other strains are commonly available. While vectors employing the 2 micron origin of replication are illustrated, Broach, J. R., *Meth Enz* (1983) 101:307, other plasmid vectors suitable for yeast expression are known (see, for example, Stinchcomb, et al., *Nature* (1979) 282:39, Tschempe, et al., *Gene* (1980)10:157 and Clark, L., et al., *Meth Enz* (1983) 101:300). Control sequences for yeast vectors include promoters for the synthesis of glycolytic enzymes (Hess, et al., *J Adv Enzyme Req* (1968) 7:149; Holland, et al. *Biochemistry* (1978) 17:4900). Additional promoters known in the art include the promoter for 3-phosphoglycerate kinase (Hitzeman, et al., *J Biol Chem* (1980) 255:2073), and those for other glycolytic enzymes such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions are the promoter regions for alcohol dehydrogenase 2, isocytochrome C, acidphosphatase, degradative enzymes associated with nitrogen metabolism, and enzymes responsible for maltose and galactose utilization (Holland, ibid). It is also believed terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M. J., et al., *J Biol Chem* (1981) 256:1385) or the LEU2 gene obtained from YEp13 (Broach, J., et al., *Gene* (1978) 8:121), however any vector containing a yeast compatible promoter, origin of replication and other control sequences is suitable.

It is also, of course, possible to express genes encoding polypeptides in eucaryotic host cell cultures derived from multicellular organisms. See, for example, *Tissue Cultures*, Academic Press, Cruz and Patterson, editors (1973). Useful host cell lines include VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) Fiers, et al., *Nature* (1978) 273:113), or other viral promoters such as those derived from polyoma, Adenovirus 2, bovine papilloma virus, or avian sarcoma viruses. General aspects of mammalian cell host system transformations have been described e.g. by Axel; U.S. Pat. No. 4,399,216. It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes. Plant cells are also now available as hosts, and control sequences compatible with plant cells such as the nopaline synthase promoter and polyadenylation signal sequences (Depicker, A., et al., *J Mol Appl Gen* (1982) 1:561) are available.

Depending on the host cell used, transformation is done using standard techniques appropriate to such cells. The calcium treatment employing calcium chloride, as described by Cohen, S. N., *Proc Natl Acad Sci* (USA) (1972) 69:2110, or methods described in *Molecular Cloning: A Laboratory Manual* (1988) Cold Spring Harbor Press, could be used for procaryotes or other cells which contain substantial cell wall barriers. Infection with *Agrobacterium tumefaciens* (Shaw, C. H., et al., *Gene* (1983) 23:315) is believed useful for certain plant cells. For mammalian cells without such cell walls, the calcium phosphate precipitation method of Graham and van der Eb, *Virology* (1978) 52:546 can be used. Transformations into yeast can be carried out according to the method of Van Solingen, P., et al., *J Bact* (1977) 130:946 and Hsiao, C. L., et al., *Broc Natl Acad Sci* (USA) (1979) 76:3829.

cDNA or genomic libraries can be screened using the colony hybridization procedure. Generally, each microtiter plate is replicated onto duplicate nitrocellulose filter papers (S&S type BA-85) and colonies are allowed to grow at 37° C. for 14–16 hr on L agar containing 50 µg/ml Amp. The colonies are lysed and DNA fixed to the filter by sequential treatment for 5 min with 500 mM NaOH, 1.5M NaCl, and are washed twice for 5 min each time with 5x standard saline citrate (SSC). Filters are air dried and baked at 80° C. for 2 hr. The duplicate filters are prehybridized at 42° C. for 6–8 hr with 10 ml per filter of DNA hybridization buffer (5×SSC, pH 7.0 5x Denhardt's solution (polyvinylpyrrolidine, plus Ficoll and bovine serum albumin; 1×=0.02% of each), 50 mM sodium phosphate buffer at pH 7.0, 0.2% SDS, 20 µg/ml Poly U, and 50 µg/ml denatured salmon sperm DNA).

The samples can be hybridized with kinased probe under conditions which depend on the stringency desired. Typical moderately stringent conditions employ a temperature of 42° C. for 24–36 hr with 1–5 ml/filter of DNA hybridization buffer containing probe. For higher stringencies high temperatures and shorter times are employed. Generally, the filters are washed four times for 30 min each time at 37° C. with 2×SSC, 0.2% SDS and 50 mM sodium phosphate buffer at pH 7, then are washed twice with 2xSSC and 0.2% SDS, air dried, and are autoradiographed at—70° C. for 2 to 3 days.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage can be performed by treating the DNA with a suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by one unit of enzyme in about 20 µl of buffer solution. Incubation times of about one hour to two hours at about 37° C. are workable, although variations can be tolerated. After each incubation, protein can be removed by extraction with phenol/chloroform, and may be followed by ether extraction, and the nucleic acid recovered from aqueous fractions by precipitation with ethanol followed by running over a Sephadex G-5 spin column. If desired, size separation of the cleaved fragments may be performed by polyacrylamide gel or agarose gel electrophoresis using standard techniques. A general description of size separations can be found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 5–10 µM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides can be prepared by the triester method of Metteucci, et al. (*J Am Chem Soc* (1981) 103:3185) or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5 mM dithiothreitol, 1–2 Mm ATP, 1.7 pmoles $\gamma^{32}P$-ATP (2.9 mCi/mmole), 0.1 mM spermidine, 0.1 mM EDTA.

Ligations can be performed in 15–30 µl volumes under the following standard conditions and temperatures: 20 mM Tris-Cl pH 7.5, 10 mM $MgCl_2$, 10 mM DTT, 33 µg/ml GSA, 10 mM–50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations (usually employing a 10–30 fold molar excess of linkers) are performed at 1 µM total ends concentration.

In vector construction employing "vector fragments", the vector fragment can be treated with bacterial alkaline phosphatase (BAP) in order to remove the 5' phosphate and prevent religation of the vector. BAP digestions can be conducted at pH 8 in approximately 150 mM Tris, in the presence of Na+ and $Mg+^2$ using about 1 unit of BAP per µg of vector at 60° C. for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis can be used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques can be hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Correct ligations for plasmid construction can be confirmed by first transforming a suitable host with the ligation mixture. Successful transformants are selected by ampicillin, tetracycline or other antibiotic resistance or using other markers depending on the mode of plasmid construction, as is understood in the art. Plasmids from the transformants can then be prepared according to the method of Clewell, D. B., et al. *Proc Natl Acad Sci* (USA) (1969) 62:1159, optionally following chloramphenicol amplification (Clewell, D. B., *J Bacteriol* (1972) 110:667). The isolated DNA Is analyzed by restriction and/or sequenced by the dideoxy method of Snager, F., et al. *Proc Natl Acad Sci* (USA) (1977) 74:5463 as further described by Messing, et al., F. Supp. *Nucleic Acids Res* (1981) 9.309, or by the method of Maxam, et al., *Methods in Enzymology* (1980) 65:499.

In accordance with the present invention polynucleotide probes specifically hybridizable to a portion of the leucine zipper protein kinase gene are provided. Polynucleotide probes substantially homologous to a portion of the leucine-zipper protein kinase gene are also provided. Such probes may be used for diagnostic or research purposes to detect or quantitate the expression of leucine zipper protein kinase in a sample such as by detecting the presence or absence of polynucleotide duplex formation between the polynucleotide probe and leucine-zipper protein kinase gene. Samples may derived from cell culture or may be derived from a patient. Samples may be biological fluids such as synovial fluid in some aspects of the invention. Tissue samples may also be used in some embodiments of the present invention. Detection of the presence of polynucleotide duplexes is indicative of the presence of the leucine-zipper protein kinase gene in a sample and may be indicative of diseases associated with leucine zipper protein kinase, such as tumors of the central nervous system. Provision of means for detecting hybridization of polynucleotides with the leucine-zipper protein kinase gene can routinely be accomplished. Such provision may include enzyme conjugation, radiolabelling or any other suitable detection systems. Kits for detecting the presence or absence of leucine zipper protein kinase or a particular transcript thereof may also be prepared. Said polynucleotide probes may range in length from about 5 to about 100 nucleotide units. In more preferred embodiments of the present invention the probes may be from about 8 to about 75 nucleotide units in length. Ideally, said probes range in length from about 12 to about 50 nucleotide units. It is recognized that since polynucleotide probes of the present invention may preferably not exceed 100 nucleotides in length, said probes may specifically hybridize to only a portion of the targeted sequence. The portion of the leucine zipper protein kinase sequence to be targeted can be identified by one skilled in the art. Most suitably, a target sequence is chosen which is unique, thereby decreasing background noise attributable to hybridization by the probe other than to the target. By way of example, one skilled in the art would be unlikely to select a repeating sequence of adenine nucleotide units as this is a common sequence occurring in many genes. The practitioner might choose to perform a search and comparison of sequences found in a sequence repository such as Genbank in order to identify and design a useful probe. Such methods of conventionally used to identify unique sequences. These unique sequences, when used as probes, need not necessarily be crucial to the regulation of the expression of leucine-zipper protein kinase.

In accordance with other methods of the present invention, neuronal cells may be contacted with leucine-zipper protein kinase, or a portion thereof in order to inhibit cellular proliferation. While not wishing to be bound to a particular theory, it is believed that the addition of exogenous leucine-zipper protein kinase, or portions thereof may interfere with specific protein-protein or protein-nucleic acid interactions involved in cellular hyperproliferation. For example, by administering an inactive leucine-zipper protein kinase polypeptide or a portion thereof, it may be possible to compete with naturally occurring leucine-zipper protein kinase for binding regions of target nucleic acid molecules or polypeptides in order to modulate its effect in the cell at the level of protein-protein or protein-nucleic acid interactions. In this way, it may be possible to treat a mammal suffering from tumors of the central nervous system by inhibiting the overexpression of leucine-zipper protein kinase in vivo or by interfering with a vital signal in the chain of signals leading to tumorigenicity.

For methods of the present invention, leucine-zipper protein kinase may be formulated into pharmacological compositions containing an effective amount of leucine-zipper protein kinase and a usual nontoxic carrier, such carriers being known to those skilled in the art. The compositions may be administered by a method suited to the form of the composition. Such compositions are, for example, in the form of usual liquid preparations including solutions, suspensions, emulsions, and the like which can be given orally, intravenously, subcutaneously or intramuscularly.

The present invention is also directed to methods of inhibiting hyperproliferation of neuronal cells comprising contacting the cells with oligonucleotides substantially complementary to a portion of the nucleic acid sequence set forth in SEQ ID NO: 1. "Complementary" in the context of this invention, means the ability to form hydrogen bonds, also known as Watson-Crick base pairing, between complementary bases, usually on opposite nucleic acid strands or two regions of a nucleic acid strand, to form a double-stranded duplex. Guanine and cytosine are examples of complementary bases which are known to form three hydrogen bonds between them. Adenine and thymine are examples of complementary bases which are known to form two hydrogen bonds between them. "Specifically hybridizable" and "substantially complementary" are terms which indicate a sufficient degree of complementarity to avoid non-specific binding of the oligonucleotide (or polynucleotide probe) to non-target sequences under conditions in which specific binding is desired, i.e., under physiological conditions in the case of in vivo assays and therapeutic treatment, or, in the case of in vitro assays, under conditions in which the assays are conducted. It is understood that an oligonucleotide or polynucleotide probe need not be 100% complementary to its target nucleic acid sequence to be specifically hybridizable or effective in methods of the present invention. In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. The oligonucleotides in accordance with this invention preferably comprise from about 5 to about 50 nucleotide units. It is more preferred that such oligonucleotides comprise from about 8 to 30 nucleotide units, and still more preferred to have from about 12 to 25 nucleotide units. Oligonucleotides of the present invention may be prepared by standard techniques such as solid-phase synthesis which are well known to those skilled in the art.

Furthermore, in accordance with methods of the present invention, a therapeutically effective amount of oligonucleotide is administered to a mammal suffering from tumors of the central nervous system.

Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotides.

The pharmaceutical compositions of the present invention may be administered in a number of ways depending on whether local or systemic treatment is desired, and on the area to be treated. Administration may be done topically (including ophthalmically, vaginally, rectally, intranasally), orally, by inhalation, or parenterally, for example by intravenous drip or subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms or gloves may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The following examples are illustrative and are not meant to be limiting of the present invention.

EXAMPLES

EXAMPLE 1

Cells

Human teratocarcinoma line NT2 was differentiated into postmitotic neurons NT2-N with retinoic acid as previously described (Pleasure et al., *J. Neurosci* 12: 1802–1815 (1992); Younkin et al., *Proc. Natl. Acad. Sci. USA* 90: 2174–2178 (1992)). Poly(A)$^+$ RNA was isolated from both NT2 and NT2-N neurons using Invitrogen mRNA kit.

EXAMPLE 2

Subtractive Hybridization and DNA Amplification

Invitrogen's Subtractor probe kit was used according to the manufacturer's instructions to isolate two different subtracted cDNAs UND and DIFF. UND was enriched in transcripts expressed in the undifferentiated stage whereas DIFF was enriched in transcripts present in the neurons. One μg portions of UND and DIFF mRNA were used for PCT amplification with degenerate primers as described in Wilks *Proc. Natl. Acad. Sci. USA* 86: 1603–1607 (1989). PCT was performed using a Geneamp kit (Cetus) with 1 μg of each of the degenerate primers. The final concentration of magnesium was 2.1 mM. PCT cycling was performed on a Perkin-Elmer 480 thermal cycler for 39 cycles with a profile of 1.3 minutes at 95° C. (denaturation), 2 minutes at 45° C. (annealing), and 2 minutes at 64° C. (elongation).

EXAMPLE 3

Subcloning of Amplified DNAs and DNA Sequencing

The PCR reaction mixture were run on 4% Nusieve agarose gel and the amplified band of ~220 bp was excised. The band was purified using Magic PCR Kit (Promega). The amplified DNA was digested with the restriction enzymes BamH1/EcoR1. The amplified DNAs were subcloned into the BamH1 and EcoR1 cleaved Bluescript DNA. A total of about 200 clones (100 representing UND and 100 representing DIFF) were examined by sequencing using a Taq DyeDeoxy terminator cycle sequencing kit (Applied Biosystems). Plasmid DNA was isolated using Qiagen column 20. The cycle sequencing reactions were performed in a Perkin-Elmer 480 thermal cycler for 25 cycles with a profile of 96° C. for 30 seconds, 40° C. for 15 seconds, and 60° C. for 4 minutes. Following separation of the extension products on a Select-D G-50 column (5 Prime 3 Prime) the reaction mixtures were dried, resuspended in 4 μl of 5:1 formamide/50 mM EDTA, loaded on a 6% sequencing gel, and analyzed using an Applied Biosystems 373 fluorescent sequencer.

EXAMPLE 4 cDNA Library Screening

The 210 bp 10.2 PCR clone from undifferentiated clones was radiolabelled with [$^{32}$P]dCTP and used to probe ~$10^6$ plaques from an amplified human fetal brain library (Stratagene) to obtain larger cDNA clones. Hybridization was carried out overnight at 42° C. in 50% Formamide, 5xSSPE, 5xDenhardt's, 1% SDS, 100ug/ml sheared salmon sperm DNA, and 1×$10^6$ cpm/ml of probe. Filters were washed at 60° C. twice in 2xSSC containing 0.1% SDS, and exposed overnight to Kodak XAR-5 film at −70° C.

EXAMPLE 5

Sequence Determination cDNAs were subcloned into a plasmid vector BluescriptSk. For complete sequence determination, unidirectional nested deletions was performed using the Exo111/Mung Bean nuclease kit from Stratagene. The colonies obtained after deletions were sequenced as described earlier using a Taq DyeDeoxy terminator cycle sequencing kit (Applied Biosystems). The DNA sequence obtained was determined after sequencing twice.

EXAMPLE 6

Sequence Comparisons

All sequence manipulations were done on a VAX using the University of Wisconsin Genetics Computer Group Sequence Analysis Software Package. DNA fragments obtained after nested deletions was assembled into Contigs using the Programme Sequencer 2.0 (Gene Codes Corp). Protein analysis was done using MacVector (IBI).

EXAMPLE 7

RNA Analysis

Human multiple tissue northern blots were purchased from Clontech laboratories. Hybridization conditions were similar to that used for library screening. Filters were washed to a final stringency of 0.1 xSSC/0.1% SDS at 65° C. before exposure to XAR-5 x-ray film.

What is claimed is:

1. cDNA coding for a human leucine-zipper protein kinass.

2. cDNA encoding a protein which is at least 85% homologous to a protein encoded by the nucleic acid sequence set forth in SEQ ID NO: 1.

3. A construct comprising a vector and the cDNA of claim 2.

4. The construct of claim 3 further comprising a promoter operably linked to said cDNA.

5. Recombinant host cells transformed with cDNA of claim 2 whereby said host cells express leucine-zipper protein kinass.

6. A method of producing leucine-zipper protein kinass which comprises culturing recombinant host cells wherein said host cells are transformed with cDNA encoding a protein which is at least 85% homologous to a protein encoded by SEQ ID NO:1 operably linked to regulatory control sequences which effect the expression of said coding sequence in said transformed host cells and isolating said leucine-zipper protein kinase produced by said host cells.

* * * * *

UNITED STATES PATENT AND TRADEMARK OFFICE
CERTIFICATE OF CORRECTION

PATENT NO. : 5,554,523
DATED : September 10, 1996
INVENTOR(S) : Reddy, et al.

It is certified that error appears in the above-indentified patent and that said Letters Patent is hereby corrected as shown below:

At Column 21, line 26 delete "kinass" and insert -- kinase -- therefor.

At Column 22, line 25 delete "kinass" and insert -- kinase -- therefor.

At Column 22, line 26, delete "kinass" and insert -- kinase -- therefor.

Signed and Sealed this

Eleventh Day of March, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3426 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 99..2105

( x i ) SEQUENCE DESCRIPTION: SEQ ID NO:1:

```
AGCATCCGGA  GCGGAGCTGC  AGCAGCGCCG  CCTTTTGTGC  TGCGGCCGCG  GAGCCCCGA              60

GGGCCCAGTG  TTCACCATCA  TACCAGGGGC  CAGAGGCG ATG GCT TGC CTC CAT                  113
                                            Met Ala Cys Leu His
                                            1               5

GAG ACC CGA ACA CCC TCT CCT TCC TTT GGG GGC TTT GTG TCT ACC CTA                  161
Glu Thr Arg Thr Pro Ser Pro Ser Phe Gly Gly Phe Val Ser Thr Leu
            10              15                  20

AGT GAG GCA TCC ATG CGC AAG CTG GAC CCA GAC ACT TCT GAC TGC ACT                  209
```

| | | | | | | | | | | | | | | | | |
|---|---|---|---|---|---|---|---|---|---|---|---|---|---|---|---|---|
| Ser | Glu | Ala | Ser<br>25 | Met | Arg | Lys | Leu | Asp<br>30 | Pro | Asp | Thr | Ser | Asp<br>35 | Cys | Thr | |
| CCC | GAG | AAG | GAC | CTG | ACG | CCT | ACC | CAT | GTC | CTG | CAG | CTA | CAT | GAG | CAG | 257 |
| Pro | Glu | Lys<br>40 | Asp | Leu | Thr | Pro | Thr<br>45 | His | Val | Leu | Gln | Leu<br>50 | His | Glu | Gln | |
| GAT | GCA | GGG | GGC | CCA | GGG | GGA | GCA | GCT | GGG | TCA | CCT | GAG | AGT | CGG | GCA | 305 |
| Asp | Ala | Gly<br>55 | Gly | Pro | Gly | Gly<br>60 | Ala | Ala | Gly | Ser | Pro<br>65 | Glu | Ser | Arg | Ala | |
| TCC | AGA | GTT | CGA | GCT | GAC | GAG | GTG | CGA | CTG | CAG | TGC | CAG | AGT | GGC | AGT | 353 |
| Ser<br>70 | Arg | Val | Arg | Ala | Asp<br>75 | Glu | Val | Arg | Leu | Gln<br>80 | Cys | Gln | Ser | Gly | Ser<br>85 | |
| GGC | TTC | CTT | GAG | GGC | CTC | TTT | GGC | TGC | CTG | CGC | CCT | GTC | TGG | ACC | ATG | 401 |
| Gly | Phe | Leu | Glu | Gly<br>90 | Leu | Phe | Gly | Cys | Leu<br>95 | Arg | Pro | Val | Trp | Thr<br>100 | Met | |
| ATT | GGC | AAA | GCC | TAC | TCC | ACT | GAG | CAC | AAG | CAG | CAG | CAG | GAA | GAC | CTT | 449 |
| Ile | Gly | Lys | Ala<br>105 | Tyr | Ser | Thr | Glu | His<br>110 | Lys | Gln | Gln | Gln | Glu<br>115 | Asp | Leu | |
| TGG | GAG | GTC | CCC | TTT | GAG | GAA | ATC | CTG | GAC | CTG | CAG | TGG | GTG | GGC | TCA | 497 |
| Trp | Glu | Val<br>120 | Pro | Phe | Glu | Glu | Ile<br>125 | Leu | Asp | Leu | Gln | Trp<br>130 | Val | Gly | Ser | |
| GGG | GCC | CAG | GGT | GCT | GTC | TTC | CTG | GGG | CGC | TTC | CAC | GGG | GAG | GAG | GTG | 545 |
| Gly | Ala | Gln<br>135 | Gly | Ala | Val | Phe<br>140 | Leu | Gly | Arg | Phe | His<br>145 | Gly | Glu | Glu | Val | |
| GCT | GTG | AAG | AAG | GTG | CGA | GAC | CTC | AAA | GAA | ACC | GAC | ATC | AAG | CAC | TTG | 593 |
| Ala<br>150 | Val | Lys | Lys | Val | Arg<br>155 | Asp | Leu | Lys | Glu | Thr<br>160 | Asp | Ile | Lys | His | Leu<br>165 | |
| CGA | AAG | CTG | AAG | CAC | CCC | AAC | ATC | ATC | ACT | TTC | AAG | GGT | GTG | TGC | ACC | 641 |
| Arg | Lys | Leu | Lys | His<br>170 | Pro | Asn | Ile | Ile | Thr<br>175 | Phe | Lys | Gly | Val | Cys<br>180 | Thr | |
| CAG | GCT | CCC | TGC | TAC | TGC | ATC | CTC | ATG | GAG | TTC | TGC | GCC | CAG | GGC | CAG | 689 |
| Gln | Ala | Pro | Cys<br>185 | Tyr | Cys | Ile | Leu | Met<br>190 | Glu | Phe | Cys | Ala | Gln<br>195 | Gly | Gln | |
| CTG | TAT | GAG | GTA | CTG | CGG | GCT | GGC | CGC | CCT | GTC | ACC | CCC | TCC | TTA | CTG | 737 |
| Leu | Tyr | Glu<br>200 | Val | Leu | Arg | Ala | Gly<br>205 | Arg | Pro | Val | Thr | Pro<br>210 | Ser | Leu | Leu | |
| GTT | GAC | TGG | TCC | ATG | GGC | ATC | GCT | GGT | GGC | ATG | AAC | TAC | CTG | CAC | CTG | 785 |
| Val | Asp | Trp<br>215 | Ser | Met | Gly | Ile<br>220 | Ala | Gly | Gly | Met | Asn<br>225 | Tyr | Leu | His | Leu | |
| CAC | AAG | ATT | ATC | CAC | AGG | GAT | CTC | AAG | TCA | CCC | AAC | ATG | CTA | ATC | ACC | 833 |
| His<br>230 | Lys | Ile | Ile | His | Arg<br>235 | Asp | Leu | Lys | Ser | Pro<br>240 | Asn | Met | Leu | Ile | Thr<br>245 | |
| TAC | GAC | GAT | GTG | GTG | AAG | ATC | TCA | GAT | TTT | GGC | ACT | TCC | AAG | GAG | CTG | 881 |
| Tyr | Asp | Asp | Val | Val<br>250 | Lys | Ile | Ser | Asp | Phe<br>255 | Gly | Thr | Ser | Lys | Glu<br>260 | Leu | |
| AGT | GAC | AAG | AGC | ACC | AAG | ATG | TCC | TTT | GCA | GGG | ACA | GTA | GCC | TGG | ATG | 929 |
| Ser | Asp | Lys | Ser<br>265 | Thr | Lys | Met | Ser | Phe<br>270 | Ala | Gly | Thr | Val | Ala<br>275 | Trp | Met | |
| GCC | CCT | GAG | GTG | ATC | CGC | AAT | GAA | CCT | GTG | TCT | GAG | AAG | GTC | GAC | ATC | 977 |
| Ala | Pro | Glu<br>280 | Val | Ile | Arg | Asn | Glu<br>285 | Pro | Val | Ser | Glu | Lys<br>290 | Val | Asp | Ile | |
| TGG | TCC | TTT | GGC | GTG | GTG | CTA | TGG | GAA | CTG | CTG | ACT | GGT | GAG | ATC | CCC | 1025 |
| Trp | Ser<br>295 | Phe | Gly | Val | Val | Leu<br>300 | Trp | Glu | Leu | Leu | Thr<br>305 | Gly | Glu | Ile | Pro | |
| TAC | AAA | GAC | GTA | GAT | TCC | TCA | GCC | ATT | ATC | TGG | GGT | GTG | GGA | AGC | AAC | 1073 |
| Tyr<br>310 | Lys | Asp | Val | Asp | Ser<br>315 | Ser | Ala | Ile | Ile | Trp<br>320 | Gly | Val | Gly | Ser | Asn<br>325 | |
| AGT | CTC | CAT | CTG | CCC | GTG | CCC | TCC | AGT | TGC | CCA | GAT | GGT | TTC | AAG | ATC | 1121 |
| Ser | Leu | His | Leu | Pro<br>330 | Val | Pro | Ser | Ser | Cys<br>335 | Pro | Asp | Gly | Phe | Lys<br>340 | Ile | |
| CTG | CTT | CGC | CAG | TGC | TGG | AAT | AGC | AAA | CCA | CGA | AAT | CGC | CCA | TCA | TTC | 1169 |

```
Leu Leu Arg Gln Cys Trp Asn Ser Lys Pro Arg Asn Arg Pro Ser Phe
        345                 350                 355

CGA CAG ATC CTG CTG CAT CTG GAC ATT GCC TCA GCT GAT GTA CTC TCC         1217
Arg Gln Ile Leu Leu His Leu Asp Ile Ala Ser Ala Asp Val Leu Ser
        360                 365                 370

ACA CCC CAG GAG ACT TAC TTT AAG TCC CAG GCA GAG TGG CGG GAA GAA         1265
Thr Pro Gln Glu Thr Tyr Phe Lys Ser Gln Ala Glu Trp Arg Glu Glu
        375                 380                 385

GTA AAA CTG CAC TTT GAA AAG ATT AAG TCA GAA GGG ACC TGT CTG CAC         1313
Val Lys Leu His Phe Glu Lys Ile Lys Ser Glu Gly Thr Cys Leu His
390             395                 400                 405

CGC CTA GAA GAG GAA CTG GTG ATG AGG AGG AGG GAG GAG CTC AGA CAC         1361
Arg Leu Glu Glu Glu Leu Val Met Arg Arg Arg Glu Glu Leu Arg His
                410                 415                 420

GCC CTG GAC ATC AGG GAG CAC TAT GAA AGG AAG CTG GAG AGA GCC AAC         1409
Ala Leu Asp Ile Arg Glu His Tyr Glu Arg Lys Leu Glu Arg Ala Asn
            425                 430                 435

AAC CTG TAT ATG GAA CTT AAT GCC CTC ATG TTG CAG CTG GAA CTC AAG         1457
Asn Leu Tyr Met Glu Leu Asn Ala Leu Met Leu Gln Leu Glu Leu Lys
        440                 445                 450

GAG AGG GAG CTG CTC AGG CGA GAG CAA GCT TTA GAG CGG AGG TGC CCA         1505
Glu Arg Glu Leu Leu Arg Arg Glu Gln Ala Leu Glu Arg Arg Cys Pro
        455                 460                 465

GGC CTG CTG AAG CCA CAC CCT TCC CGG GGC CTC CTG CAT GGA AAC ACA         1553
Gly Leu Leu Lys Pro His Pro Ser Arg Gly Leu Leu His Gly Asn Thr
470             475                 480                 485

ATG GAG AAG CTT ATC AAG AAG AGG AAT GTG CCA CAG AAT CTG TCA CCC         1601
Met Glu Lys Leu Ile Lys Lys Arg Asn Val Pro Gln Asn Leu Ser Pro
                490                 495                 500

CAT AGC CAA AGG CCA GAT ATC CTC AAG GCG GAG TCT TTG CTC CCT AAA         1649
His Ser Gln Arg Pro Asp Ile Leu Lys Ala Glu Ser Leu Leu Pro Lys
            505                 510                 515

CTA GAT GCA GCC CTG AGT GGG GTG GGG CTT CCT GGG TGT CCT AAG GCC         1697
Leu Asp Ala Ala Leu Ser Gly Val Gly Leu Pro Gly Cys Pro Lys Ala
        520                 525                 530

CCC CCC TCA CCA GGA CGG AGT CGC CGT GGC AAG ACC CGT CAC CGC AAG         1745
Pro Pro Ser Pro Gly Arg Ser Arg Arg Gly Lys Thr Arg His Arg Lys
535             540                 545

GCC AGC GCC AAG GGG AGC TGT GGG GAC CTG CCT GGG CTT CGT ACA GCT         1793
Ala Ser Ala Lys Gly Ser Cys Gly Asp Leu Pro Gly Leu Arg Thr Ala
550             555                 560                 565

GTG CCA CCC CAT GAA CCT GGA GGA CCA GGA AGC CCA GGG GCT CTA GGA         1841
Val Pro Pro His Glu Pro Gly Gly Pro Gly Ser Pro Gly Gly Leu Gly
                570                 575                 580

GGG GGA CCC TCA GCC TGG GAG GCC TGC CCT CCC GCC CTC CGT GGG CTT         1889
Gly Gly Pro Ser Ala Trp Glu Ala Cys Pro Pro Ala Leu Arg Gly Leu
            585                 590                 595

CAT CAT GAC CTC CTC CTC CGC AAA ATG TCT TCA TCG TCC CCA GAC CTG         1937
His His Asp Leu Leu Leu Arg Lys Met Ser Ser Ser Ser Pro Asp Leu
        600                 605                 610

CTG TCA GCA GCA CTA GGG TCC CGG GGC CGG GGG GCC ACA GGC GGA GCT         1985
Leu Ser Ala Ala Leu Gly Ser Arg Gly Arg Gly Ala Thr Gly Gly Ala
615             620                 625

GGG GAT CCT GGC TCA CCA CCT CCG GCC CGG GGT GAC ACC CCA CCA AGT         2033
Gly Asp Pro Gly Ser Pro Pro Pro Ala Arg Gly Asp Thr Pro Pro Ser
630             635                 640                 645

GAG GGC TCA CCC CCT GGC TCC ACC AGC CCA GAT TCA CCT GGG GAG CCA         2081
Glu Gly Ser Pro Pro Gly Ser Thr Ser Pro Asp Ser Pro Gly Glu Pro
                650                 655                 660

AAG GGG AAC CAC CTC CTC CAG TAGGGCCTGG TGAAGGTGTG GGGCTTCTGG            2132
```

```
            Lys  Gly  Asn  His  Leu  Leu  Gln
                       665

GAACTGGAAG  GGAAGGGACC  TCAGGCCGGG  GAGGAAGCCG  GGCTGGGTCC  CAGCACTTGA   2192

CCCCATCTGC  ACTGCTGTAC  AGGGCTGCCG  TCACCCGAAG  TCAGAAACGT  GGCATCTCAT   2252

CGGAAGAGGA  GGAAGGAGAG  GTAGACAGTG  AAGTAGAGCT  GACATCAAGC  AGAGGTGGC    2312

CTCAGAGCCT  GAACATGCGC  CAGTCACTAT  CTACCTTCAG  CTCAGAGAAT  CCATCAGATG   2372

GGGAGGAAGG  CACAGCTAGT  GAACCTTCCC  CCAGTGGCAC  ACCTGAAGTT  GGCAGCACCA   2432

ACACTGATGA  GCGGCCAGAT  GAGCGGTCTG  ATGACATGTG  CTCCCAGGGC  TCAGAAATCC   2492

CACTGGACCC  ACCTCCTTCA  GAGGTCATCC  CTGGCCCTGA  ACCCAGCTCC  CTGCCCATTC   2552

CACACCAGGA  ACTTCTCAGA  GAGCGGGGCC  CTCCCAATTC  TGAGGACTCA  GACTGTGACA   2612

GCACTGAATT  GGACAACTCC  AACAGCGTTG  ATGCCTTGCG  CCCCCCAGCT  TCCCTCCCTC   2672

CATGAAAGCC  ACTCGTATTC  CTTGTACATA  GAGAAATATT  TATATGGATT  ATATATATAT   2732

ACATATATAT  ATATATATGC  GCCACATAAT  CAACAGAAAG  ATGGGGCTGT  CCCAGCCGTA   2792

AGTCAGGCTC  GAGGGAGACT  GATCCCCTGA  CCAATTCACC  TGATAAACTC  TAGGGACACT   2852

GGCAGCTGTG  GAAATGAATG  AGGCACAGCC  GTAGAGCTGT  GGCTAAGGGC  AAGCCCCTTC   2912

CTGCCCCACC  CCATTCCTTA  TATTCAGCAA  GCAACAAGGC  AATAGAAAAG  CCAGGGTTGT   2972

CTTTATATTC  TTTATCCCCA  AATAATAGGG  GGTGGGGGGA  GGGGCGGTGG  GAGGGGCAGG   3032

AGAGAAAACC  ACTTAGACTG  CACTTTTCTG  TTCCGTTTAC  TCTGTTTACA  CATTTTGCAC   3092

TTGGGAGGAG  GGAGGCTAAG  GCTGGGTCCT  CCCCTCTGAG  GTTTCTCAGG  TGGCAATGTA   3152

ACTCATTTTT  TTGTCCCACC  ATTTATCTTC  TCTGCCCAAG  CCCTGTCTTA  AGGCCCAGGG   3212

GGAGGTTAGG  AGACTGATAG  CATGTGATGG  CTCAGGCTGA  AGAACCGGGG  TTCTGTTTAA   3272

GTCCCTGCTT  TTATCCTGGT  GCCTGATTGG  GGTGGGGACT  GTCCTACTGT  AACCCCTGTG   3332

AAAAACCTTG  AAAAATAACA  CTCCATGCAG  GAAAAAAAAA  AAAAAAAAA   AAAAAGGAA    3392

TTCGATATCA  AGCTTATCGA  TACCGTCGAC  CTCG                                3426
```

( 2 ) INFORMATION FOR SEQ ID NO:2:

( i ) SEQUENCE CHARACTERISTICS:
        ( A ) LENGTH: 668 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Cys  Leu  His  Glu  Thr  Arg  Thr  Pro  Ser  Pro  Ser  Phe  Gly  Gly
 1                  5                        10                       15

Phe  Val  Ser  Thr  Leu  Ser  Glu  Ala  Ser  Met  Arg  Lys  Leu  Asp  Pro  Asp
                20                       25                       30

Thr  Ser  Asp  Cys  Thr  Pro  Glu  Lys  Asp  Leu  Thr  Pro  Thr  His  Val  Leu
                35                       40                       45

Gln  Leu  His  Glu  Gln  Asp  Ala  Gly  Gly  Pro  Gly  Gly  Ala  Ala  Gly  Ser
                50                       55                       60

Pro  Glu  Ser  Arg  Ala  Ser  Arg  Val  Arg  Ala  Asp  Glu  Val  Arg  Leu  Gln
 65                      70                       75                       80

Cys  Gln  Ser  Gly  Ser  Gly  Phe  Leu  Glu  Gly  Leu  Phe  Gly  Cys  Leu  Arg
                     85                       90                       95

Pro  Val  Trp  Thr  Met  Ile  Gly  Lys  Ala  Tyr  Ser  Thr  Glu  His  Lys  Gln
                100                      105                      110
```

-continued

| | | | | | | | | | | | | | | |
|---|---|---|---|---|---|---|---|---|---|---|---|---|---|---|
| Gln | Gln | Glu 115 | Asp | Leu | Trp | Glu 120 | Val | Pro | Phe | Glu | Glu 125 | Ile | Leu | Asp | Leu |
| Gln | Trp 130 | Val | Gly | Ser | Gly 135 | Ala | Gln | Gly | Ala | Val 140 | Phe | Leu | Gly | Arg | Phe |
| His 145 | Gly | Glu | Glu | Val | Ala 150 | Val | Lys | Lys | Val | Arg 155 | Asp | Leu | Lys | Glu | Thr 160 |
| Asp | Ile | Lys | His | Leu 165 | Arg | Lys | Leu | Lys | His 170 | Pro | Asn | Ile | Ile | Thr 175 | Phe |
| Lys | Gly | Val | Cys 180 | Thr | Gln | Ala | Pro | Cys 185 | Tyr | Cys | Ile | Leu | Met 190 | Glu | Phe |
| Cys | Ala | Gln 195 | Gly | Gln | Leu | Tyr | Glu 200 | Val | Leu | Arg | Ala | Gly 205 | Arg | Pro | Val |
| Thr | Pro 210 | Ser | Leu | Leu | Val | Asp 215 | Trp | Ser | Met | Gly | Ile 220 | Ala | Gly | Gly | Met |
| Asn 225 | Tyr | Leu | His | Leu | His 230 | Lys | Ile | Ile | His | Arg 235 | Asp | Leu | Lys | Ser | Pro 240 |
| Asn | Met | Leu | Ile | Thr 245 | Tyr | Asp | Asp | Val | Val 250 | Lys | Ile | Ser | Asp | Phe 255 | Gly |
| Thr | Ser | Lys | Glu 260 | Leu | Ser | Asp | Lys | Ser 265 | Thr | Lys | Met | Ser | Phe 270 | Ala | Gly |
| Thr | Val | Ala 275 | Trp | Met | Ala | Pro | Glu 280 | Val | Ile | Arg | Asn | Glu 285 | Pro | Val | Ser |
| Glu | Lys 290 | Val | Asp | Ile | Trp | Ser 295 | Phe | Gly | Val | Val | Leu 300 | Trp | Glu | Leu | Leu |
| Thr 305 | Gly | Glu | Ile | Pro | Tyr 310 | Lys | Asp | Val | Asp | Ser 315 | Ser | Ala | Ile | Ile | Trp 320 |
| Gly | Val | Gly | Ser | Asn 325 | Ser | Leu | His | Leu | Pro 330 | Val | Pro | Ser | Ser | Cys 335 | Pro |
| Asp | Gly | Phe | Lys 340 | Ile | Leu | Leu | Arg | Gln 345 | Cys | Trp | Asn | Ser | Lys 350 | Pro | Arg |
| Asn | Arg | Pro 355 | Ser | Phe | Arg | Gln | Ile 360 | Leu | Leu | His | Leu | Asp 365 | Ile | Ala | Ser |
| Ala | Asp 370 | Val | Leu | Ser | Thr | Pro 375 | Gln | Glu | Thr | Tyr | Phe 380 | Lys | Ser | Gln | Ala |
| Glu 385 | Trp | Arg | Glu | Glu | Val 390 | Lys | Leu | His | Phe | Glu 395 | Lys | Ile | Lys | Ser | Glu 400 |
| Gly | Thr | Cys | Leu | His 405 | Arg | Leu | Glu | Glu | Glu 410 | Leu | Val | Met | Arg | Arg 415 | Arg |
| Glu | Glu | Leu | Arg 420 | His | Ala | Leu | Asp | Ile 425 | Arg | Glu | His | Tyr | Glu 430 | Arg | Lys |
| Leu | Glu | Arg 435 | Ala | Asn | Asn | Leu | Tyr 440 | Met | Glu | Leu | Asn | Ala 445 | Leu | Met | Leu |
| Gln | Leu 450 | Glu | Leu | Lys | Glu | Arg 455 | Glu | Leu | Leu | Arg | Arg 460 | Glu | Gln | Ala | Leu |
| Glu 465 | Arg | Arg | Cys | Pro | Gly 470 | Leu | Leu | Lys | Pro | His 475 | Pro | Ser | Arg | Gly | Leu 480 |
| Leu | His | Gly | Asn | Thr 485 | Met | Glu | Lys | Leu | Ile 490 | Lys | Lys | Arg | Asn | Val 495 | Pro |
| Gln | Asn | Leu | Ser 500 | Pro | His | Ser | Gln | Arg 505 | Pro | Asp | Ile | Leu | Lys 510 | Ala | Glu |
| Ser | Leu | Leu 515 | Pro | Lys | Leu | Asp | Ala 520 | Ala | Leu | Ser | Gly | Val 525 | Gly | Leu | Pro |
| Gly | Cys 530 | Pro | Lys | Ala | Pro | Pro 535 | Ser | Pro | Gly | Arg | Ser 540 | Arg | Arg | Gly | Lys |

| | | | | | | | | | | | | | | |
|---|---|---|---|---|---|---|---|---|---|---|---|---|---|---|
| Thr 545 | Arg | His | Arg | Lys | Ala 550 | Ser | Ala | Lys | Gly | Ser 555 | Cys | Gly | Asp | Leu | Pro 560 |
| Gly | Leu | Arg | Thr | Ala 565 | Val | Pro | Pro | His | Glu 570 | Pro | Gly | Gly | Pro | Gly 575 | Ser |
| Pro | Gly | Gly | Leu 580 | Gly | Gly | Gly | Pro | Ser 585 | Ala | Trp | Glu | Ala | Cys 590 | Pro | Pro |
| Ala | Leu | Arg 595 | Gly | Leu | His | His | Asp 600 | Leu | Leu | Leu | Arg | Lys 605 | Met | Ser | Ser |
| Ser | Ser 610 | Pro | Asp | Leu | Leu | Ser 615 | Ala | Ala | Leu | Gly | Ser 620 | Arg | Gly | Arg | Gly |
| Ala 625 | Thr | Gly | Gly | Ala | Gly 630 | Asp | Pro | Gly | Ser | Pro 635 | Pro | Pro | Ala | Arg | Gly 640 |
| Asp | Thr | Pro | Pro | Ser 645 | Glu | Gly | Ser | Pro | Pro 650 | Gly | Ser | Thr | Ser | Pro 655 | Asp |
| Ser | Pro | Gly | Glu 660 | Pro | Lys | Gly | Asn | His 665 | Leu | Leu | Gln | | | | |